(12) United States Patent
Cadwell

(10) Patent No.: US 6,933,144 B2
(45) Date of Patent: *Aug. 23, 2005

(54) APPARATUS FOR GROWING CELLS

(75) Inventor: John J. S. Cadwell, New Market, MD (US)

(73) Assignee: Fibercell Systems, Inc., New Market, MD (US)

(*) Notice: Subject to any disclaimer, the term of this patent is extended or adjusted under 35 U.S.C. 154(b) by 76 days.

This patent is subject to a terminal disclaimer.

(21) Appl. No.: 10/436,991

(22) Filed: May 14, 2003

(65) Prior Publication Data

US 2003/0203478 A1 Oct. 30, 2003

Related U.S. Application Data

(62) Division of application No. 09/885,920, filed on Jun. 22, 2001, now Pat. No. 6,566,126.

(51) Int. Cl.$^7$ ................................................ C12M 1/00
(52) U.S. Cl. ................. 435/297.4; 435/325; 435/283.1; 435/289.1; 435/297.1; 435/304.1; 435/383
(58) Field of Search ......................... 435/297.4, 325, 435/283.1, 289.1, 297.1, 304.1, 297, 383; 424/94.1

(56) References Cited

U.S. PATENT DOCUMENTS

| | | | |
|---|---|---|---|
| 3,883,393 A | 5/1975 | Knazek et al. | 195/1.8 |
| 4,144,136 A | 3/1979 | Corbeil | 195/127 |
| 4,225,671 A | 9/1980 | Puchinger et al. | 435/71 |
| 4,391,912 A | 7/1983 | Yoshida et al. | 435/241 |
| 4,546,083 A | 10/1985 | Meyers et al. | 435/240 |
| 4,647,539 A | 3/1987 | Bach | 435/284 |
| 4,661,458 A | 4/1987 | Berry et al. | 435/284 |
| 4,717,668 A | 1/1988 | Keilman et al. | 435/296 |
| 4,962,033 A | 10/1990 | Serkes et al. | 435/240.243 |
| 5,079,168 A | 1/1992 | Amiot | 437/284 |
| 5,290,700 A | 3/1994 | Binot et al. | 435/284 |
| 5,416,022 A | 5/1995 | Amiot | 435/284 |
| 5,426,037 A | 6/1995 | Pannell et al. | 435/70.21 |
| 5,449,617 A | 9/1995 | Falkenberg et al. | 435/240.25 |
| 5,576,211 A | 11/1996 | Falkenberg et al. | 435/297.1 |
| 5,650,325 A | 7/1997 | Spielmann | 435/299.1 |
| 5,686,301 A | 11/1997 | Falkenberg et al. | 435/297.1 |
| 5,693,537 A | 12/1997 | Wilson et al. | 435/401 |
| 5,702,945 A | 12/1997 | Nagels et al. | 435/297.1 |
| 5,707,869 A | 1/1998 | Wolf et al. | 435/401 |
| 5,714,384 A | 2/1998 | Wilson et al. | 435/401 |
| 5,955,353 A | 9/1999 | Amiot | 435/297.4 |
| 6,190,913 B1 | 2/2001 | Singh | 435/394 |
| 6,544,788 B2 | 4/2003 | Singh | 435/383 |

FOREIGN PATENT DOCUMENTS

JP         63102667 A         5/1998

OTHER PUBLICATIONS

*Innovations in Biotechnology*, at http://www.wavebiotech.com, 2 pages (last visited Oct. 9, 2001).
*Introducing the Wave Bioreactor*, at http://www.wavebiotech.com/WBOverview.htm, 2 pages (last visited Oct. 9, 2001).
*Wave Bioreactor Applications*, at http://www.wavebiotech.com/WBApplications.htm, 2 pages (last visited Oct. 9, 2001).
*Wave Bioreactor Selection Guide*, at http://www.wavebiotech.com/WBSelectionGuide.htm, 2 pages (last visited Oct. 9, 2001).
*Wave Bioreactor Specifications*, at http://www.wavebiotech.com/WBSpecifications.htm, 2 pages (last visited Oct. 9, 2001).
*Wave Bioreactor FAQ's and Tips*, at http://www.wavebiotech.com/WBFAQ.htm, 1 page (last visited Oct. 9, 2001).
*Wave Bioreactor Literature*, at http://www.wavebiotech.com/WBLiterature.htm, 2 pages (last visited Oct. 9, 2001).
*How to Order a Wave Bioreactor*, at http://www.wavebiotech.com/WBOrder.htm, 2 pages (last visited Oct. 9, 2001).
*Overview*, http://www.wavebiotech.com/Slideshows/bioreactor%20slides2002_files/outline.htm, 1 page (last visited Oct. 3, 2001).

*Primary Examiner*—Leon B. Lankford, Jr.
*Assistant Examiner*—Ruth A. Davis
(74) *Attorney, Agent, or Firm*—Sterne, Kessler, Goldstein & Fox P.L.L.C.

(57) ABSTRACT

A cell-culture apparatus forms an extra-capillary space between at least one hollow fiber and an enclosed chamber. Cells are placed in the extra-capillary space to grow. A media reservoir holds a cell-culture medium. The cell-culture medium is allowed to pass through a lumen of the at least one hollow fiber and to pass nutrients through the walls of the at least one hollow fiber to the cells in the extra-capillary space. Flow through the at least one hollow fiber is produced by action of gravity when a rocking or rotating motion is imparted to the media reservoir.

9 Claims, 4 Drawing Sheets

600

602
ACCESS THE MEDIA RESERVOIR TO SUPPLY CELL-CULTURE MEDIA

604
PLACE CELLS INTO THE EXTRA-CAPILLARY SPACE FORMED BETWEEN THE SEMIPERMEABLE CAPILLARY TUBES AND THE ENCLOSED CHAMBER

606
ROCK THE MEDIA RESERVOIR BACK AND FORTH TO CAUSE A FLOW OF THE CELL-CULTURE MEDIA TO PASS THROUGH THE LUMENS OF THE CAPILLARY TUBES BY ACTION OF GRAVITY, WHEREBY THE CELL-CULTURE MEDIA PASSES NUTRIENTS THROUGH THE WALLS OF THE CAPILLARY TUBES TO NOURISH THE CELLS IN THE EXTRA-CAPILLARY SPACE

608
ACCESS THE EXTRA-CAPILLARY SPACE TO REMOVE THE CELLS

610
ACCESS THE MEDIA RESERVOIR TO REMOVE CELL-CULTURE MEDIA AND ANY WASTE PRODUCTS

FIG.6

APPARATUS FOR GROWING CELLS

CROSS-REFERENCE TO RELATED APPLICATIONS

This application is a division of U.S. application Ser. No. 09/885,920, filed Jun. 22, 2001, now U.S. Pat. No. 6,566,126.

BACKGROUND OF THE INVENTION

1. Field of the Invention

The invention described herein relates to an apparatus and a method for growing suspension and adherent cells in vitro.

2. Background Art

Growing living cells in vitro is performed for a variety of purposes, including the production of cell derivatives, the preparation of viral vaccines, and the recovery of valuable cell by-products. Among the devices that have been developed for growing cells in vitro, the shell-and-tube type arrangement has become fairly common, particularly for growing suspension and adherent cells.

These devices use semipermeable tube-shaped hollow fibers (i.e., capillaries), contained within an outer shell, and configured so that fluid within a space external to the hollow fibers (i.e., an extra-capillary space) is segregated from fluid passing through the hollow fibers and their corresponding openings (i.e., lumens). Additionally, these devices usually include two manifold end chambers within the outer shell on opposite ends of the device. Each of the two lumens of a hollow fiber connects to a different end chamber. The end chambers and the extra-capillary space are separated by the semi-permeable membranes of the hollow fibers. The composition of the extra-capillary space can be controlled, to a certain extent, by the molecular weight cutoff, or pore size, of the membranes of the hollow fibers.

Typically, cells are grown in the extra-capillary space while a nutrient media is passed through the hollow fibers. The semipermeable nature of the hollow fibers allows nutrients and cell waste products to pass through the walls of the hollow fibers while blocking cells from doing the same. U.S. Pat. No. 4,391,912 to Yoshida et al. specifies a range of pore diameters to support the transfer of the nutrient medium from the intra-capillary to the extra-capillary space while blocking the entrance of cells into the intra-capillary space.

Shell-and-tube type bioreactors provide several advantages. For adherent cells, the use of several hollow fibers provides, within a relatively small volume, a large amount of surface area upon which the cells can grow. For both suspension and adherent cells, this large amount of surface area also facilitates localized distribution of nutrient media to the growing cells and ready collection of cell waste products. Shell-and-tube type bioreactors enable the growth of cells at much higher density rates than is possible with other cell culture devices. They can support cell densities greater than $10^8$ cells per milliliter, whereas other cell culture devices are typically limited to densities around $10^6$ cells per milliliter.

However, existing designs typically require external support systems to circulate the nutrient media through the hollow fibers. U.S. Pat. No. 3,883,393 to Knazek et al., U.S. Pat. No. 4,144,136 to Corbeil, U.S. Pat. No. 4,391,912 to Yoshida et al., U.S. Pat. No. 5,290,700 to Binot et al., and U.S. Pat. No. 5,955,353 to Amiot, all teach systems in which the nutrient medium is supplied to the intra-capillary spaces using pumps and associated connection tubing. These external circulating systems add considerably to the cost of using these types of shell-and-tube bioreactors.

What is needed is a shell-and-tube type apparatus to grow suspension and adherent cells that does not require an external circulating system for the nutrient media fluid.

BRIEF SUMMARY OF THE INVENTION

The present invention describes an apparatus and method for growing cells. An extra-capillary space is formed between hollow fibers and an enclosed chamber. Cells are placed in the extra-capillary space to grow. A media reservoir holds cell-culture media. The cell-culture media is allowed to pass through a lumen of the hollow fibers and to pass nutrients through the walls of the hollow fibers to the cells in the extra-capillary space. Flow through the hollow fibers is produced by action of gravity when a rocking motion is imparted to the media reservoir or by action of gravity when the media reservoir is rotated about a horizontal axis.

Preferably, the hollow fibers are made of a semi-permeable material. The semi-permeable material allows: (1) nutrients and (2) metabolizing gasses to pass from the cell-culture media through the walls of the hollow fibers to the cells in the extra-capillary space, and (3) cell waste products and (4) gaseous waste products to pass from the extra-capillary space through the walls of the hollow fibers to the cell-culture media, while retaining the cells and large secreted products within the extra-capillary space.

Preferably, the media reservoir further includes a membrane permitting gas exchange between an exterior and an interior of the media reservoir.

Preferably, the media reservoir includes a first opening for accessing the interior of the media reservoir. The first opening allows: (1) fresh cell-culture media to be supplied to the media reservoir, (2) stale cell-culture media to be removed from the media reservoir, and (3) cell waste products to be removed from the media reservoir.

In one embodiment, the enclosed chamber is disposed within the media reservoir. An extra-chamber space is defined between the media reservoir and the enclosed chamber. Each hollow fiber has, at each end, a lumen open to the extra-chamber space. Preferably, the media reservoir includes a second opening for accessing the extra-capillary space. The second opening allows: (1) developing cells to be placed into the extra-capillary space, (2) mature cells to be removed from the extra-capillary space, (3) secreted products to be harvested, and (4) the cells to be treated with reagents, drugs, and/or DNA or RNA vectors.

In another embodiment, the media reservoir is configured to cause a flow of the cell-culture media between a first port and a second port. The enclosed chamber is connected between the first and second ports. Each hollow fiber has, at each end, a lumen open to the flow of the cell-culture media between the first and second ports. Preferably, the enclosed chamber includes a second opening for accessing the extra-capillary space. The second opening allows: (1) developing cells to be placed into the extra-capillary space, and (2) mature cells to be removed from the extra-capillary space.

Further features and advantages of the invention as well as the structure and operation of various embodiments of the present invention are described in detail below with reference to the accompanying drawings.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the pertinent art to make and use the invention.

FIG. 6 is a flowchart illustrating the method 600 of the present invention.

The preferred embodiments of the invention are described with reference to the figures where like reference numbers indicate identical or functionally similar elements. Also in the figures, the left most digit of each reference number identifies the figure in which the reference number is first used.

DETAILED DESCRIPTION OF THE INVENTION

Figure 1:
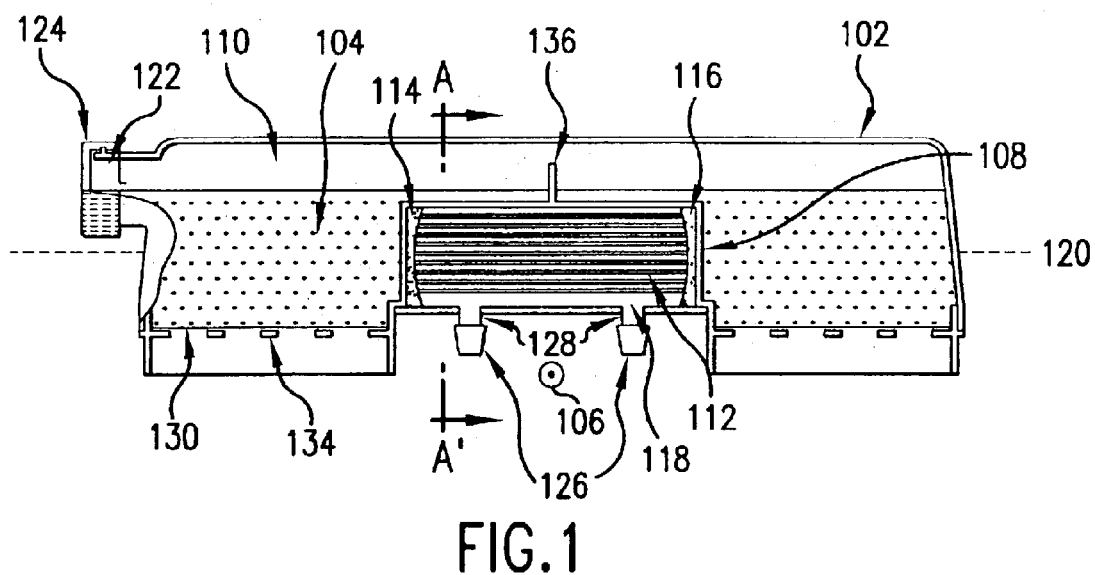
FIG. 1 is a cutaway, cross sectional side view of a preferred embodiment of the apparatus of the present invention.

FIG. 1 is a cutaway, cross sectional side view of a preferred embodiment of the apparatus of the present invention. In FIG. 1, a media reservoir 102 holds cell-culture media 104 and is configured to be rocked or rotated about a horizontal axis of rotation 106 that extends into the drawing sheet of FIG. 1. An enclosed chamber 108 is disposed within media reservoir 102, wherein an extra-chamber space 110 is defined between media reservoir 102 and enclosed chamber 108.

A plurality of hollow fibers 112 pass through enclosed chamber 108 and are secured at each end by a first potting structure 114 and a second potting structure 116. An extra-capillary space 118 is defined between an interior of enclosed chamber 108 and the exterior surfaces of the hollow fibers 112. The hollow fibers 112 are oriented substantially parallel to a longitudinal axis 120, which is substantially perpendicular to horizontal axis of rotation 106.

In a representative embodiment of the invention, 25 to 200 hollow fibers 112 are disposed within enclosed chamber 108. The length of the hollow fibers 112 is from about 3 to 10 centimeters, and the diameter is from about 200 to 1,000 microns. Preferably, hollow fibers 112 have a length-to-diameter ratio of less than about 170:1 to reduce the head loss of cell-culture media 104 that passes through them. Because the present invention relies on action of gravity to cause the flow of cell-culture media 104, it is preferred that the hollow fibers 112 have a length-to-diameter ratio small enough to allow a sufficient rate of flow through them. Cumulatively, hollow fibers 112 can support a cell-culture media flow rate from about 5 to 100 milliliters per minute and have a surface area from about 25 to 1,000 square centimeters. However, one skilled in the art would recognize embodiments of the present invention with both a greater and a fewer number of hollow fibers 112 (including as few as one hollow fiber 112) and with different parameters defining them.

Figure 2:
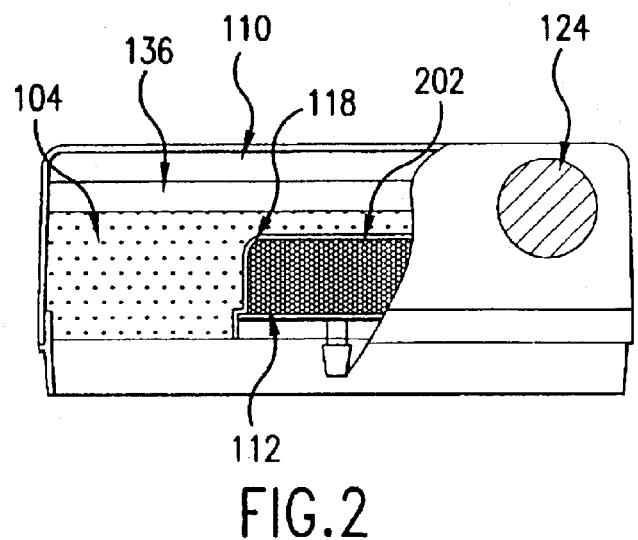
FIG. 2 is a cutaway end view showing a partial cross section of the embodiment shown in FIG. 1 taken along section A–A'.

FIG. 2 is a cutaway end view showing a partial cross section of the embodiment shown in FIG. 1 taken along section A–A'. In FIG. 2, each hollow fiber 112 has, at each end, a lumen 202 open to extra-chamber space 110 such that cell-culture media 104 can pass through the lumen 202 of hollow fiber 112 and pass nutrients through the walls of hollow fiber 112 to nourish the cells in the extra-capillary space 118.

Preferably, each hollow fiber 112 is made of a semi-permeable material. The semi-permeable material allows: (1) nutrients and (2) metabolizing gasses to pass from the cell-culture media 104 through the walls of the hollow fibers 112 to the cells in the extra-capillary space 118, and (3) cell waste products and (4) gaseous waste products to pass from extra-capillary space 118 through the walls of the hollow fibers 112 to cell-culture media 104, while retaining the cells and large secreted products within extra-capillary space 118. Consumption of nutrients and metabolizing gasses by the cells establishes a gradient between extra-chamber space 110 and extra-capillary space 118. The gradient causes nutrients and gasses to diffuse through the walls of the hollow fibers 112 and into extra-capillary space 118. Conversely, a build up of cell waste products and gaseous waste products in the extra-capillary space 118 establishes a reverse gradient between extra-capillary space 118 and extra-chamber space 110. This reverse gradient causes these waste products to diffuse through the walls of the hollow fibers 112 into the lumens 202 and finally into extra-chamber space 110.

Preferably, in one embodiment, the semi-permeable material has pores with diameters no larger than 0.2 microns. In various embodiments, the semi-permeable material can be made of one or more of polysulfone, modified polysulfone, polyvinyledine fluoride, cellulose acetate, acrylic copolymer, and a cellulose derivative, wherein said cellulose derivative is one or more of a mixed ester of cellulose and cupra-ammonium rayon. However, one skilled in the art will recognize that other materials can be used for the semi-permeable material.

Returning to FIG. 1, media reservoir 102 preferably includes an opening 122 for accessing extra-chamber space 110. Opening 122 allows: (1) fresh cell-culture media to be supplied to media reservoir 102, (2) stale cell-culture media to be removed from media reservoir 102, and (3) cell waste products to be removed from media reservoir 102. A lid 124 is used to seal opening 122.

Preferably, media reservoir 102 includes an opening 126 for accessing extra-capillary space 118. In an embodiment, opening 126 includes a port 128 passing through extra-chamber space 110 to provide access to extra-capillary space 118. Opening 126 allows: (1) developing cells to be placed into extra-capillary space 118, (2) mature cells to be removed from extra-capillary space 118, (3) secreted products to be harvested, and (4) the cells to be treated with reagents, drugs, and/or DNA or RNA vectors. In an embodiment, media reservoir 102 includes more than one opening 126.

Preferably, media reservoir 102 further includes a gas permeable membrane 130 permitting gas exchange between an environment exterior to media reservoir 102 and extra-chamber space 110. As discussed above, gasses are exchanged between extra-chamber space 110 and extra-capillary space 118 through the walls of hollow fibers 112. Membrane 130 permits the exchange of the waste gasses from extra-chamber space 110 with fresh gasses from the environment exterior to media reservoir 102. Transverse members 134 provide support and structural integrity to media reservoir 102 along a face that includes membrane 130. In one embodiment, membrane 130 is made of silicone. However, one skilled in the art will recognize that other materials can be used for the membrane.

A dam 136 is disposed in media reservoir 102 to impede flow of cell-culture media 104 in extra-chamber space 110 when media reservoir 102 is rocked or rotated about horizontal axis of rotation 106. Dam 136 also serves to encourage flow of cell-culture media 104 through the hollow fibers 112. In an embodiment in which enclosed chamber 108 spans the width of media reservoir 102 along horizontal axis of rotation 106, enclosed chamber 108 and dam 136 are integrated.

Figure 3:
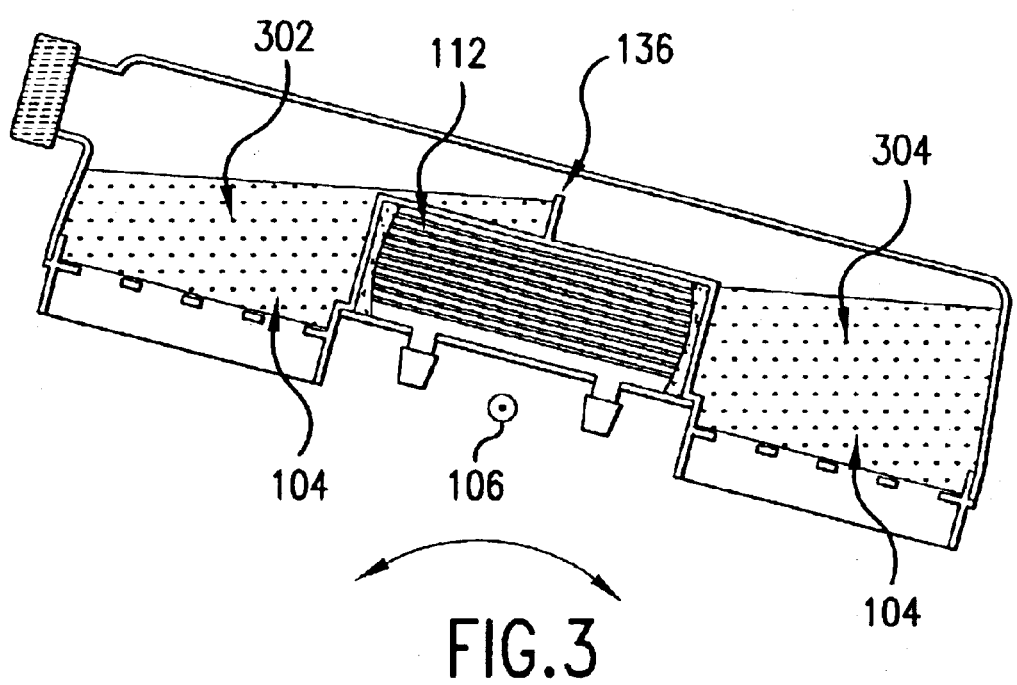
FIG. 3 is similar to FIG. 1, but illustrates how a rocking motion causes the flow of the cell-culture media.

FIG. 3 is similar to FIG. 1, but illustrates how a rocking or rotating motion causes the flow of cell-culture media. In FIG. 3, one skilled in the art will recognize how dam 136, by impeding the flow of cell-culture media 104 in extra-chamber space 110, simultaneously increases the static head pressure of a raised portion 302 of cell-culture media 104 and decreases the static head pressure of a lowered portion 304 of cell-culture media 104 that would otherwise exist in the absence of dam 134. Thus, by increasing the differential pressure across the hollow fibers 112, dam 136 serves to encourage flow of cell-culture media 104 through the hollow fibers 112.

Figure 4:
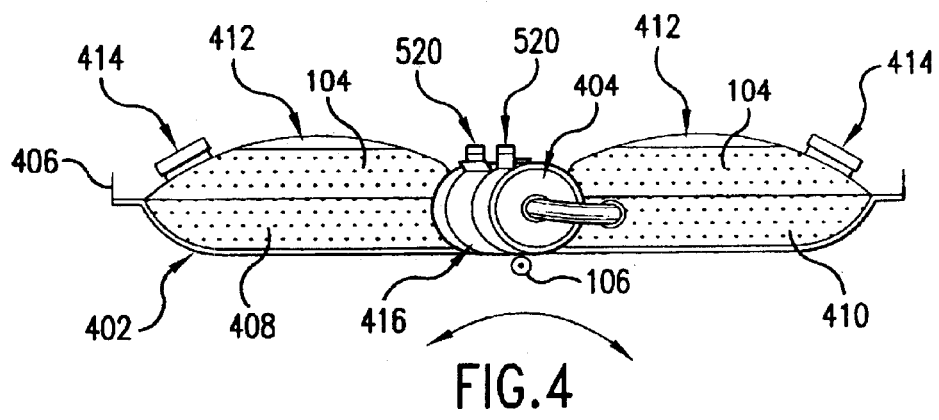
FIG. 4 is a side view of an alternative preferred embodiment of the apparatus of the present invention.
Figure 5:
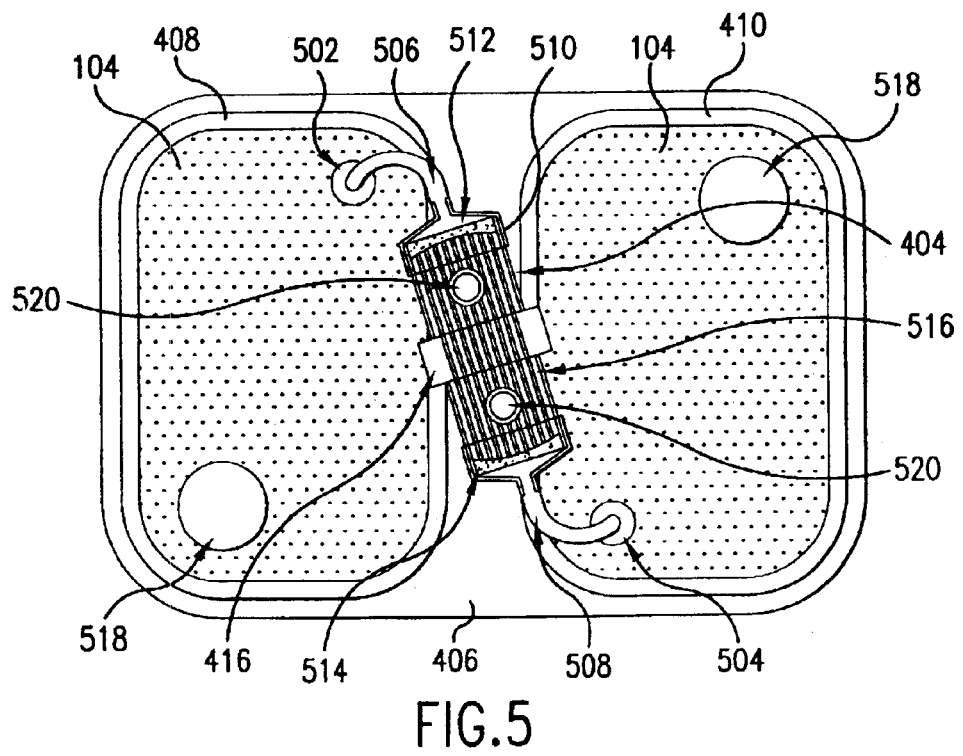
FIG. 5 shows a top view of the embodiment shown in FIG. 4.

FIG. 4 is a side view of an alternative preferred embodiment of the apparatus of the present invention. FIG. 5 shows a top view of the embodiment shown in FIG. 4. In FIGS. 4 and 5, a media reservoir 402 holds cell-culture media 104 and is configured to cause a flow of cell-culture media 104 between a first port 502 and a second port 504 in response to a rocking or rotating motion imparted to media reservoir 402. An enclosed chamber 404 is connected between first port 502 and second port 504. One skilled in the art will recognize that these connections can be realized by several means including, but not limited to, a first tubing section 506 connected between first port 502 and enclosed chamber 404, and a second tubing section 508 connected between second port 504 and enclosed chamber 404.

A plurality of hollow fibers 510 passes through enclosed chamber 404 and is secured at each end by a first potting structure 512 and a second potting structure 514. An extra-capillary space 516 is defined between an interior of the enclosed chamber 404 and the exterior surfaces of the hollow fibers 510. Each hollow fiber 510 has, at each end, a lumen open to the flow of cell-culture media 104 between first port 502 and second port 504 such that cell-culture media 104 can pass through the lumen of hollow fiber 510 and pass nutrients through the walls of hollow fiber 510 to nourish the cells in extra-capillary space 516. Other functions and parameters of the hollow fibers 510 are identical to those included in the first preferred embodiment described above.

In a representative embodiment of the invention, 25 to 200 hollow fibers 510 are disposed within enclosed chamber 404. The length of the hollow fibers 510 is from about 3 to 10 centimeters, and the diameter is from about 200 to 1,000 microns. Preferably, hollow fibers 510 have a length-to-diameter ratio of less than about 170:1 to reduce the head loss of cell-culture media 104 that passes through them. Because the present invention relies on action of gravity to cause the flow of cell-culture media 104, it is preferred that the hollow fibers 510 have a length-to-diameter ratio small enough to allow a sufficient rate of flow through them. Cumulatively, hollow fibers 510 can support a cell-culture media flow rate from about 5 to 100 milliliters per minute and have a surface area from about 25 to 1,000 square centimeters. However, one skilled in the art would recognize embodiments of the present invention with both a greater and a fewer number of hollow fibers 510 (including as few as one hollow fiber 510) and with different parameters defining them.

Enclosed chamber 404 can be a standard, commercially available shell-and-tube type bioreactor designed for use with an external circulating system.

Preferably, media reservoir 402 comprises a tray 406, a first bag 408 connected to first port 502, and a second bag 410 connected to second port 504. This configuration serves to encourage flow of cell-culture media 104 through the hollow fibers 510 when a rocking or rotating motion is imparted to media reservoir 402. Advantageously, this configuration allows for flexibility in the orientation of hollow fibers 510 with respect to horizontal axis of rotation 106. However, one skilled in the art will recognize other embodiments by which media reservoir 402 can be realized. These include, but are not limited to, a configuration using one bag connected to both ports, wherein the bag includes a damming or dividing mechanism to encourage flow of cell-culture media 104 through enclosed chamber 404 by increasing the differential pressure between the two ports when the bag is rocked or rotated.

In an embodiment, first bag 408 and second bag 410 are made of a gas permeable material such as silicone permitting gas exchange between the environment exterior to media reservoir 102 and an interior 414 of media reservoir 402. In an alternate embodiment, only a portion of bags 408, 410 are made from a gas permeable material. Similar to the process discussed above, gasses are exchanged between an interior 412 of media reservoir 402 and extra-capillary space 516 through the walls of hollow fibers 510. The gas permeable material permits the exchange of the waste gasses from the interior 412 of media reservoir 402 with fresh gasses from the environment exterior to media reservoir 402.

Preferably, media reservoir 402 includes an opening 518 for accessing interior 412 of media reservoir 402. As described above, opening 518 allows: (1) fresh cell-culture media to be supplied to media reservoir 402, (2) stale cell-culture media to be removed from media reservoir 402, and (3) cell waste products to be removed from media reservoir 402. A lid 414 is used to seal opening 518. Where media reservoir 402 comprises first bag 408 and second bag 410, each bag has its own opening 518.

Preferably, enclosed chamber 404 includes an opening 520 for accessing extra-capillary space 516. As described above, opening 520 allows: (1) developing cells to be placed into extra-capillary space 516, (2) mature cells to be removed from extra-capillary space 516, (3) secreted products to be harvested, and (4) the cells to be treated with reagents, drugs, and/or DNA or RNA vectors. In an embodiment, enclosed chamber 404 includes more than one opening 520.

In an embodiment, enclosed chamber 404 is attached to tray 406 by a clip 416. However, one skilled in the art would recognize other means by which enclosed chamber 404 could be held in an appropriate position with respect to media reservoir 402.

FIG. 6 is a flowchart illustrating the method 600 of the present invention. In FIG. 6, at a step 602, the media reservoir is accessed to supply cell-culture media. Where cell-culture media has previously been supplied to the media reservoir, one skilled in the art will recognize that step 602 can be omitted. At a step 604, cells are placed into the extra-capillary space formed between the semipermeable hollow fibers and the enclosed chamber. At a step 606, the media reservoir is rocked back and forth to cause a flow of the cell-culture media to pass through the lumens of the hollow fibers by action of gravity. Alternatively, at step 606, the media reservoir can be rotated about a horizontal axis of rotation to cause a flow of the cell-culture media to pass through the lumens of the hollow fibers by action of gravity. The cell-culture media pass nutrients through the walls of the hollow fibers to nourish the cells in the extra-capillary space. In an embodiment, the hollow fibers are oriented substantially perpendicular to the horizontal axis of rotation.

Optionally, at a step 608, the extra-capillary space is accessed to remove the cells. Optionally, at a step 610, the media reservoir is accessed to remove the cell-culture media and any waste products.

Conclusion

While various embodiments of the present invention have been described above, it should be understood that they have been presented by way of example, and not limitation. It will be apparent to persons skilled in the relevant art that various changes in form and detail can be made therein without departing from the spirit and scope of the invention. Thus the present invention should not be limited by any of the above-described exemplary embodiments, but should be defined only in accordance with the following claims and their equivalents.

What is claimed is:

1. An apparatus for growing cells, comprising:
    a media reservoir (or holding cell-culture media and configured to be rocked or rotated about a horizontal axis of rotation;
    an enclosed chamber disposed within said media reservoir, wherein an extra-chamber space is defined between said media reservoir and said enclosed chamber; and
    at least one hollow fiber passing through said enclosed chamber, wherein each said at least one hollow fiber is substantially oriented upon a longitudinal axis substantially perpendicular to said horizontal axis of rotation, wherein each said at least one hollow fiber has, at each end, a lumen open to said extra-chamber space, and wherein an extra-capillary space is defined between an interior of said enclosed chamber and an exterior surface of said at least one hollow fiber.

2. The apparatus of claim 1, further comprising:
    a first opening in said media reservoir for accessing said extra-chamber space; and
    a second opening in said media reservoir for accessing said extra-capillary space.

3. The apparatus of claim 1, wherein said at least one hollow fiber comprises a plurality of hollow fibers.

4. The apparatus of claim 3, wherein each of said plurality of hollow fibers is made of a semi-permeable material.

5. The apparatus of claim 4, wherein said semi-permeable material is one or more of polysulfone, modified polysulfone, polyvinyledine fluoride, cellulose acetate, acrylic copolymer, and a cellulose derivative, wherein said cellulose derivative is one or more of a mixed ester of cellulose and cupra-ammonium rayon.

6. The apparatus of claim 5, wherein said semi-permeable material has pores with diameters no larger than 0.2 $\mu$m.

7. The apparatus of claim 1, wherein said media reservoir comprises a membrane permitting gas exchange between an exterior of said media reservoir and said extra-chamber space.

8. The apparatus of claim 7, wherein said membrane is made of silicone.

9. The apparatus of claim 1, further comprising:
    a dam disposed in said media reservoir to impede flow of said media in said extra-chamber space when said media reservoir is rocked or rotated about said horizontal axis of rotation and to encourage flow of said media through said at least one hollow fiber.

* * * * *